United States Patent
Norris

(10) Patent No.: US 11,534,437 B2
(45) Date of Patent: *Dec. 27, 2022

(54) METHODS OF TREATING RADIATION INDUCED GASTROINTESTINAL SYNDROME (RIGS) AND RELATED DISEASE STATES USING COMPOUND 512

(71) Applicant: BCN Biosciences L.L.C., Inglewood, CA (US)

(72) Inventor: Andrew J. Norris, Los Angeles, CA (US)

(73) Assignee: BCN Biosciences L.L.C., Inglewood, CA (US)

( * ) Notice: Subject to any disclaimer, the term of this patent is extended or adjusted under 35 U.S.C. 154(b) by 101 days.

This patent is subject to a terminal disclaimer.

(21) Appl. No.: 16/736,805

(22) Filed: Jan. 7, 2020

(65) Prior Publication Data

US 2021/0205298 A1 Jul. 8, 2021
US 2022/0047581 A9 Feb. 17, 2022

Related U.S. Application Data

(62) Division of application No. 16/058,943, filed on Aug. 8, 2018, now abandoned.

(60) Provisional application No. 62/542,647, filed on Aug. 8, 2017.

(51) Int. Cl.
*A61K 31/495* (2006.01)
*A61P 43/00* (2006.01)

(52) U.S. Cl.
CPC ............ *A61K 31/495* (2013.01); *A61P 43/00* (2018.01)

(58) Field of Classification Search
CPC .............................. A61K 31/495; A61P 43/00
See application file for complete search history.

(56) References Cited

PUBLICATIONS

Kruttika Bhat, et al., 1-[(4-Nitrophenyl)sulfonyl]-4-phenylpiperazine increases the number of Peyer's patch-associated regenerating crypts in the small intestines after radiation injury, Radiotherapy and Oncology 132 (2019) 8-15 (Year: 2019).*

* cited by examiner

*Primary Examiner* — Kortney L. Klinkel
*Assistant Examiner* — Jason Deck
(74) *Attorney, Agent, or Firm* — Entralta P.C.; James F. Fleming; Peter D. Weinstein

(57) ABSTRACT

The present disclosure is directed to method of treatment for treating or ameliorating various conditions caused by radiation exposure such as RIGS, enteritis, mucositis, e.g., oral mucositis, and proctitis by the administration of compound 512, or an analog thereof.

12 Claims, 4 Drawing Sheets

METHODS OF TREATING RADIATION INDUCED GASTROINTESTINAL SYNDROME (RIGS) AND RELATED DISEASE STATES USING COMPOUND 512

RELATED APPLICATIONS

This application is a divisional application of U.S. patent application Ser. No. 16/058,943 and claims priority and is entitled to the filing date of U.S. provisional patent application Ser. No. 62/542,647 filed on Aug. 8, 2017. The contents of the aforementioned application are incorporated herein by reference.

BACKGROUND

The risk of large populations encountering radiation exposure is real and growing due to the proliferation of rogue non state actors, political instability resulting in potential access of nuclear weapons by terrorist, and by natural disaster as evidenced by the release of radioactive material from the Fukushima nuclear power plant in early 2011. Total body exposure to radiation results acute radiation syndromes describing a clinical condition with multi organ syndrome. Radiation doses less than 8 Gy primarily develops hematopoietic injury and can be treated with supportive care with antibiotics, hydration and bone marrow transplantation. Doses of more than 10 Gy primarily leads to gastrointestinal injury resulting diarrhea, dehydration, sepsis and intestinal bleeding with eventual mortality within 10 to 15 days post-exposure. High doses of radiation induces the loss of intestinal stem cells (ISC) and thereby impairs epithelial regeneration. The damaged intestinal epithelium significantly reduces the mucosal integrity and promotes systemic influx of bacterial pathogens, resulting sepsis and death. These lethal gastrointestinal symptoms after radiation exposure are collectively known as radiation-induced gastrointestinal syndrome (RIGS).

There are few FDA approved radio-protectors able to ameliorate RIGS if applied prior to radiation exposure. However, no drugs are available which can mitigate RIGS when administered hours or days post irradiation. Considering the logistical barrier and unavoidable delay to treat victims in large casualty settings there is a tremendous need of such therapeutic measures which can be effective even if started days after radiation incident.

Dose dependent radiation damage to the intestinal stem cell is the primary cause of RIGS. It has been reported previously that inhibition of radiation induced ISC loss mitigates RIGS. This recent study demonstrated that extracellular vesicle (EV) mediated delivery of WNT rescues ISCs from radiation toxicity and induces intestinal epithelial repair with the activation of WNT-β catenin signaling. Wnt/β-catenin signaling plays a major role in ISC self-renewal and proliferation and thereby maintenance of intestinal epithelial homeostasis and repair. WNT ligands bind to LRP5/6 and Frizzled co-receptors present on epithelial crypt cells, leading to β-catenin stabilization and nuclear translocation where it binds to the nuclear transcription factor TCF4 to drive a gene-expression program that supports stem cell maintenance, proliferation and differentiation. Activation of WNT/β-catenin signaling is also crucial for crypt regeneration following injury. Several reports have demonstrated that Respondin 1 (RSPO1), an ISC growth factor and LGR5 receptor agonist, activates WNT/βcatenin pathway to repair and regenerate the intestine following chemo-radiation-induced injury. DKK1, a negative regulator WNT/β-catenin pathway, impairs the RSPO1-induced intestinal regeneration. LGR5 receptor is associated with Frizzled/Lrp Wnt receptor complex. Genetic deletion of Lgr5 in mouse intestinal inhibits Rspo1 mediated signaling but can be rescued by Wnt pathway activation.

The small molecular agent 512 (1-[(4-nitrobenezene) sulfonyl]-4-phenyl piperazine) mitigates RIGS and improves survival when applied after lethal dose of radiation exposure, preferably within or after 24 hours of exposure.

Compound 512 is an agonist of Wnt/βcatenin signaling and mitigates radiation induced intestinal injury by accelerating repair and regeneration of ISCs. Thus, 512 is also useful in mitigating radiation-induced syndromes related to RIGS and ISC rescue, such as mucositis, e.g., oral mucositis, enteritis, and proctitis. These syndromes are also often an unwanted side-effect of radiation therapy for cancer and can be treated using compound 512.

SUMMARY

In one embodiment, the invention provides a method of treating radiation induced gastrointestinal syndrome (RIGS) in a subject in need thereof, the method comprising the step of administering to the subject a therapeutically effective amount of a compound of Formula IIA or an analog thereof.

In another embodiment, the invention provides a method of treating radiation induced mucositis in a subject in need thereof, the method comprising the step of administering to the subject a therapeutically effective amount of a compound of Formula IIA or an analog thereof.

In another embodiment, the invention provides a method of treating radiation-induced proctitis in a subject in need thereof, the method comprising the step of administering to the subject a therapeutically effective amount of a compound of Formula IIA or an analog thereof.

In another embodiment, the invention provides a method of treating radiation induced enteritis in a subject in need thereof, the method comprising the step of administering to the subject a therapeutically effective amount of a compound of Formula IIA or an analog thereof.

In another embodiment, the invention provides a method of treating radiation induced hematopoietic syndrome in a subject in need thereof, the method comprising the step of administering to the subject a therapeutically effective amount of a compound of Formula IIA or an analog thereof.

In one embodiment, the compound is administered to the subject within 48 hours of the radiation exposure. In one embodiment, the compound is administered to the subject after 24 hours of the radiation exposure.

In one embodiment, the analog is selected from the group consisting of the compounds of Formula IIB-E. In one embodiment, the compound is Formula IIA.

In one embodiment, the subject received radiation therapy.

BRIEF DESCRIPTION OF THE DRAWINGS

The accompanying drawings illustrate aspects of the present invention.

Figure 1:
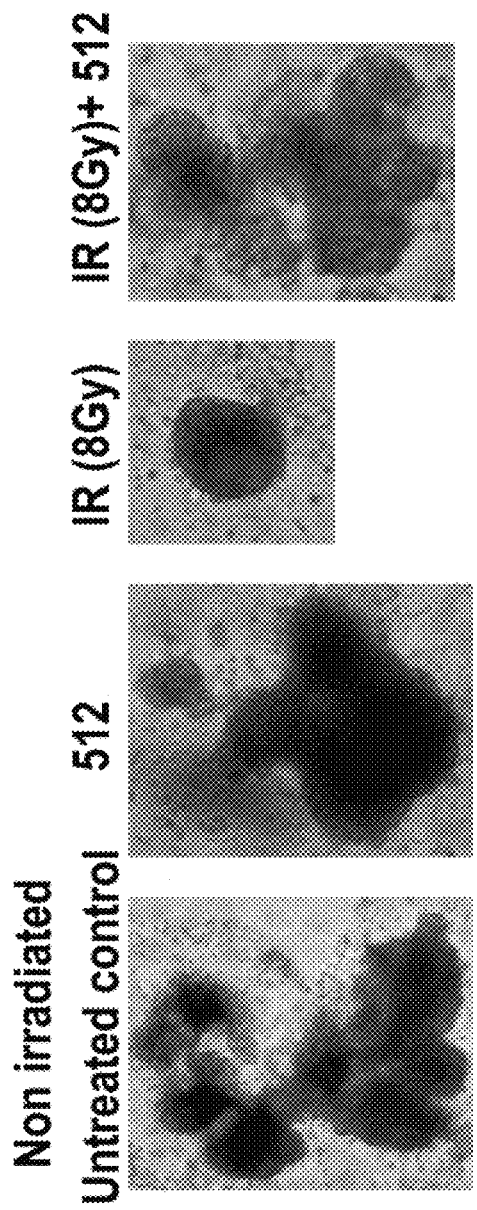
FIG. 1 is a view of a histogram of organoids in response to radiation exposure and treatment with 512 after radiation exposure.

The above described drawing figures illustrate aspects of the invention in at least one of its exemplary embodiments, which are further defined in detail in the following description. Features, elements, and aspects of the invention that are referenced by the same numerals in different figures represent the same, equivalent, or similar features, elements, or aspects, in accordance with one or more embodiments.

DETAILED DESCRIPTION

Radiation Induced Gastro Intestinal Syndrome (RIGS) limits the survival of victims in a mass casualty setting from nuclear accidents or terrorism. Currently there is no approved therapy for protecting or mitigating RIGS resulting from direct cytocidal effects on intestinal stem cells. Compound "512," an anti-neoplastic small molecular agent, activates Wnt-β catenin signaling, a key-signaling pathway for intestinal epithelial homeostasis and regeneration. Therefore, 512 is useful as an agent for mitigation of RIGS. Furthermore, 512 mitigates radiation induced mucositis, enteritis and proctitis. It is also useful for treating or preventing these radiation syndromes associated with radiation therapy. Analogs of 512 are also useful in the methods of the invention.

Radiation enteritis is a malfunction of the large and small bowel that occurs during or after radiation therapy to the abdomen, pelvis, or rectum. Severity varies, with approximately 15-20% of patients requiring an altered therapeutic course. It is usually self-limiting, often resolves within 3 months and frequently only requires supportive measures (Do et al. (2011) Gastroenterol Res Practice 2011: 917941). Chronic small bowel radiation disease typically develops between 18 months and 6 years after a completed course of radiotherapy but has been reported to present up to 30 years later (Kountouras and Zavos (2008) World J Gastroenterol 14: 7289-7301). It is a more common entity than many doctors think: 90% of patients who receive pelvic radiotherapy develop a permanent change in their bowel habits (Olopade et al. (2005) Br J Cancer 92: 1663-1670). It is also problematic, 50% of patients with pelvic irradiation describe their quality of life has been adversely affected by a variety of GI symptoms with 20-40% (depending on tumor type) rating the effect on quality of life as moderate or severe (Widmark et al., (1994) Cancer 74: 2520-2532; Crook, et al., (1996) URL 47: 387-394; Gami, et al. (2003) Aliment Pharmacol Therapeut 18(10), pp. 987-994; and Andreyev (2007 Clin Oncol 19: 790-799).

Mucositis, including oral mucositis, is probably the most common, debilitating complication of cancer treatments, particularly chemotherapy and radiation. It can lead to a number of problems, including pain, nutritional problems as a result of inability to eat, and increased risk of infection due to open sores in the mucosa. It has a significant effect on the patient's quality of life and can be dose-limiting (i.e., requiring a reduction in subsequent chemotherapy doses).

Radiation enteritis is caused by the inflammation of the small and/or large intestine from radiation treatments in the belly, sexual organs, or rectum, including treatment for cervical, pancreatic, prostate, uterine, colon and rectal cancer. Proctitis is a related radiation induced inflammation of the rectum.

The structure of compound 512 is shown below as Formula IIA:

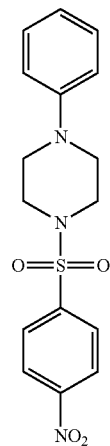

Compound 512 is also known as 1-[(4-nitrobenezene) sulfonyl]-4-phenyl piperazine. Analogs of 512 include compounds of Formula IIB:

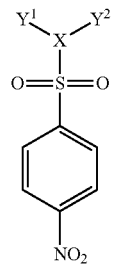

wherein:

$Y^1$ and $Y^2$ taken together with X form:

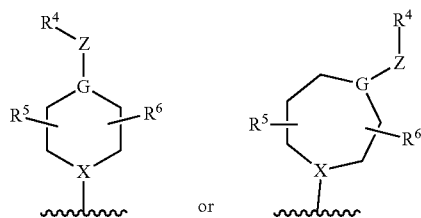

and wherein:

X is N;

G is N;

Z is absent or selected from substituted or unsubstituted alkyl, heteroalkyl, alkenyl, or alkynyl;

$R^4$ is absent or selected from substituted or unsubstituted aryl; and $R^5$ and $R^6$ are each independently absent or lower alkyl.

In one embodiment, the analog is selected from Formulae IIC-E:

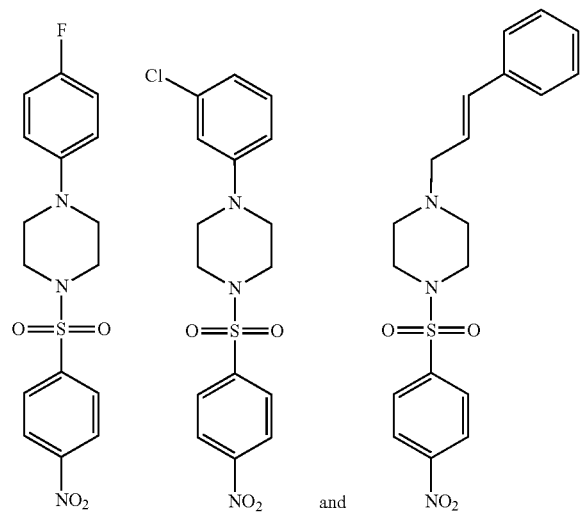 [SMILES: O=[N+]([O-])c1ccc(S(=O)(=O)N2CCN(c3ccc(F)cc3)CC2)cc1 ; O=[N+]([O-])c1ccc(S(=O)(=O)N2CCN(c3cccc(Cl)c3)CC2)cc1 ; "and" ; O=[N+]([O-])c1ccc(S(=O)(=O)N2CCN(C/C=C/c3ccccc3)CC2)cc1]

A compound of Formula IIA, or an analog thereof disclosed herein, can be prepared according to established methodology in the art of organic synthesis. General methods of synthesizing the compound can be found in, e.g., Stuart Warren and Paul Wyatt, Workbook for Organic Synthesis: The Disconnection Approach, second Edition, Wiley, 2010. Exemplary methods of making the compound is provided in U.S. Ser. No. 13/813,923 and U.S. Ser. No. 14/889,719, herein incorporated by reference in their entirety. The compound also includes a pharmaceutically acceptable salt thereof, a prodrug thereof, a hydrate thereof, a solvate thereof, or a polymorphic crystal thereof. The compound may be administered as a pharmaceutical composition.

The present methods may prevent a disease or condition or one or more symptoms of a disease or condition. As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic (i.e., it protects the host against developing the unwanted condition), whereas if it is administered after manifestation of the unwanted condition, the treatment is therapeutic (i.e., it is intended to diminish, ameliorate, or stabilize the existing unwanted condition or side effects thereof).

The compositions and methods of the present invention may be utilized to treat an individual in need thereof. In certain embodiments, the individual is a mammal such as a human, or a non-human mammal. When administered to an animal, such as a human, the composition or the compound is preferably administered or used as a pharmaceutical composition comprising, for example, a compound of the invention and a pharmaceutically acceptable carrier.

Pharmaceutically acceptable carriers are well known in the art and include, for example, aqueous solutions such as water or physiologically buffered saline or other solvents or vehicles such as glycols, glycerol, oils such as olive oil, or injectable organic esters. In a preferred embodiment, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophilized for reconstitution, powder, solution, syrup, suppository, injection or the like. The composition can also be present in a transdermal delivery system, e.g., a skin patch.

A pharmaceutical composition disclosed herein may comprise a therapeutic compound in an amount sufficient to allow customary administration to an individual. In certain embodiments, a pharmaceutical composition disclosed herein may comprise, e.g., at least 5 mg, at least 10 mg, at least 15 mg, at least 20 mg, at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 85 mg, at least 90 mg, at least 95 mg, or at least 100 mg of a therapeutic compound. In certain embodiments, a pharmaceutical composition disclosed herein may comprise, e.g., at least 5 mg, at least 10 mg, at least 20 mg, at least 25 mg, at least 50 mg, at least 75 mg, at least 100 mg, at least 200 mg, at least 300 mg, at least 400 mg, at least 500 mg, at least 600 mg, at least 700 mg, at least 800 mg, at least 900 mg, at least 1,000 mg, at least 1,100 mg, at least 1,200 mg, at least 1,300 mg, at least 1,400 mg, or at least 1,500 mg of a therapeutic compound. In yet other aspects of this embodiment, a pharmaceutical composition disclosed herein may comprise in the range of, e.g., about 5 mg to about 100 mg, about 10 mg to about 100 mg, about 50 mg to about 150 mg, about 100 mg to about 250 mg, about 150 mg to about 350 mg, about 250 mg to about 500 mg, about 350 mg to about 600 mg, about 500 mg to about 750 mg, about 600 mg to about 900 mg, about 750 mg to about 1,000 mg, about 850 mg to about 1,200 mg, or about 1,000 mg to about 1,500 mg. In still certain embodiments, a pharmaceutical composition disclosed herein may comprise in the range of, e.g., about 10 mg to about 250 mg, about 10 mg to about 500 mg, about 10 mg to about 750 mg, about 10 mg to about 1,000 mg, about 10 mg to about 1,500 mg, about 50 mg to about 250 mg, about 50 mg to about 500 mg, about 50 mg to about 750 mg, about 50 mg to about 1,000 mg, about 50 mg to about 1,500 mg, about 100 mg to about 250 mg, about 100 mg to about 500 mg, about 100 mg to about 750 mg, about 100 mg to about 1,000 mg, about 100 mg to about 1,500 mg, about 200 mg to about 500 mg, about 200 mg to about 750 mg, about 200 mg to about 1,000 mg, about 200 mg to about 1,500 mg, about 5 mg to about 1,500 mg, about 5 mg to about 1,000 mg, or about 5 mg to about 250 mg.

A pharmaceutical composition disclosed herein may comprise a solvent, emulsion or other diluent in an amount sufficient to dissolve a therapeutic compound disclosed herein. In certain embodiments, a pharmaceutical composition disclosed herein may comprise a solvent, emulsion or a diluent in an amount of, e.g., less than about 90% (v/v), less than about 80% (v/v), less than about 70% (v/v), less than about 65% (v/v), less than about 60% (v/v), less than about 55% (v/v), less than about 50% (v/v), less than about 45% (v/v), less than about 40% (v/v), less than about 35% (v/v), less than about 30% (v/v), less than about 25% (v/v), less than about 20% (v/v), less than about 15% (v/v), less than about 10% (v/v), less than about 5% (v/v), or less than about 1% (v/v). In certain embodiments, a pharmaceutical composition disclosed herein may comprise a solvent, emulsion or other diluent in an amount in a range of, e.g., about 1% (v/v) to 90% (v/v), about 1% (v/v) to 70% (v/v), about 1% (v/v) to 60% (v/v), about 1% (v/v) to 50% (v/v), about 1% (v/v) to 40% (v/v), about 1% (v/v) to 30% (v/v), about 1% (v/v) to 20% (v/v), about 1% (v/v) to 10% (v/v), about 2% (v/v) to 50% (v/v), about 2% (v/v) to 40% (v/v), about 2% (v/v) to 30% (v/v), about 2% (v/v) to 20% (v/v), about 2% (v/v) to 10% (v/v), about 4% (v/v) to 50% (v/v), about 4% (v/v) to 40% (v/v), about 4% (v/v) to 30% (v/v), about 4% (v/v) to 20% (v/v), about 4% (v/v) to 10% (v/v), about 6% (v/v) to 50% (v/v), about 6% (v/v) to 40% (v/v), about 6% (v/v) to 30% (v/v), about 6% (v/v) to 20% (v/v), about 6% (v/v) to 10% (v/v), about 8% (v/v) to 50% (v/v), about 8% (v/v) to 40% (v/v), about 8% (v/v) to 30% (v/v), about 8% (v/v) to 20% (v/v), about 8% (v/v) to 15% (v/v), or about 8% (v/v) to 12% (v/v).

The final concentration of a therapeutic compound disclosed herein in a pharmaceutical composition disclosed herein may be of any suitable concentration. In certain embodiments, the final concentration of a therapeutic compound in a pharmaceutical composition may be a therapeutically effective amount. In certain embodiments, the final concentration of a therapeutic compound in a pharmaceutical composition may be, e.g., at least 0.00001 mg/mL, at least 0.0001 mg/mL, at least 0.001 mg/mL, at least 0.01 mg/mL, at least 0.1 mg/mL, at least 1 mg/mL, at least 10 mg/mL, at least 25 mg/mL, at least 50 mg/mL, at least 100 mg/mL, at least 200 mg/mL, at least 500 mg/mL, at least 700 mg/mL, at least 1,000 mg/mL, or at least 1,200 mg/mL. In certain embodiments, the concentration of a therapeutic compound disclosed herein in the solution may be, e.g., at most 1,000 mg/mL, at most 1,100 mg/mL, at most 1,200 mg/mL, at most 1,300 mg/mL, at most 1,400 mg/mL, at most 1,500 mg/mL, at most 2,000 mg/mL, at most 2,000 mg/mL, or at most 3,000 mg/mL. In certain embodiments, the final concentration of a therapeutic compound in a pharmaceutical composition may be in a range of, e.g., about 0.00001 mg/mL to about 3,000 mg/mL, about 0.0001 mg/mL to about 3,000 mg/mL, about 0.01 mg/mL to about 3,000 mg/mL, about 0.1 mg/mL to about 3,000 mg/mL, about 1 mg/mL to about 3,000 mg/mL, about 250 mg/mL to about 3,000 mg/mL, about 500 mg/mL to about 3,000 mg/mL, about 750 mg/mL to about 3,000 mg/mL, about 1,000 mg/mL to about 3,000 mg/mL, about 100 mg/mL to about 2,000 mg/mL, about 250 mg/mL to about 2,000 mg/mL, about 500 mg/mL to about 2,000 mg/mL, about 750 mg/mL to about 2,000 mg/mL, about 1,000 mg/mL to about 2,000 mg/mL, about 100 mg/mL to about 1,500 mg/mL, about 250 mg/mL to about 1,500 mg/mL, about 500 mg/mL to about 1,500 mg/mL, about 750 mg/mL to about 1,500 mg/mL, about 1,000 mg/mL to about 1,500 mg/mL, about 100 mg/mL to about 1,200 mg/mL, about 250 mg/mL to about 1,200 mg/mL, about 500 mg/mL to about 1,200 mg/mL, about 750 mg/mL to about 1,200 mg/mL, about 1,000 mg/mL to about 1,200 mg/mL, about 100 mg/mL to about 1,000 mg/mL, about 250 mg/mL to about 1,000 mg/mL, about 500 mg/mL to about 1,000 mg/mL, about 750 mg/mL to about 1,000 mg/mL, about 100 mg/mL to about 750 mg/mL, about 250 mg/mL to about 750 mg/mL, about 500 mg/mL to about 750 mg/mL, about 100 mg/mL to about 500 mg/mL, about 250 mg/mL to about 500 mg/mL, about 0.00001 mg/mL to about 0.0001 mg/mL, about 0.00001 mg/mL to about 0.001 mg/mL, about 0.00001 mg/mL to about 0.01 mg/mL, about 0.00001 mg/mL to about 0.1 mg/mL, about 0.00001 mg/mL to about 1 mg/mL, about 0.001 mg/mL to about 0.01 mg/mL, about 0.001 mg/mL to about 0.1 mg/mL, about 0.001 mg/mL to about 1 mg/mL, about 0.001 mg/mL to about 10 mg/mL, or about 0.001 mg/mL to about 100 mg/mL.

In certain embodiments, a therapeutically effective amount of a therapeutic compound disclosed herein generally is in the range of about 0.001 mg/kg/day to about 100 mg/kg/day. In certain embodiments, an effective amount of a therapeutic compound disclosed herein may be, e.g., at least 0.001 mg/kg/day, at least 0.01 mg/kg/day, at least 0.1 mg/kg/day, at least 1.0 mg/kg/day, at least 5.0 mg/kg/day, at least 10 mg/kg/day, at least 15 mg/kg/day, at least 20 mg/kg/day, at least 25 mg/kg/day, at least 30 mg/kg/day, at least 35 mg/kg/day, at least 40 mg/kg/day, at least 45 mg/kg/day, or at least 50 mg/kg/day. In certain embodiments, an effective amount of a therapeutic compound disclosed herein may be in the range of, e.g., about 0.001 mg/kg/day to about 10 mg/kg/day, about 0.001 mg/kg/day to about 15 mg/kg/day, about 0.001 mg/kg/day to about 20 mg/kg/day, about 0.001 mg/kg/day to about 25 mg/kg/day, about 0.001 mg/kg/day to about 30 mg/kg/day, about 0.001 mg/kg/day to about 35 mg/kg/day, about 0.001 mg/kg/day to about 40 mg/kg/day, about 0.001 mg/kg/day to about 45 mg/kg/day, about 0.001 mg/kg/day to about 50 mg/kg/day, about 0.001 mg/kg/day to about 75 mg/kg/day, about 0.001 mg/kg/day to about 100 mg/kg/day, about 0.001 mg/kg/day to about 150 mg/kg/day, about 0.001 mg/kg/day to about 200 mg/kg/day, about 0.001 mg/kg/day to about 250 mg/kg/day, about 0.001 mg/kg/day to about 300 mg/kg/day, about 0.001 mg/kg/day to about 350 mg/kg/day, about 0.001 mg/kg/day to about 400 mg/kg/day, about 0.001 mg/kg/day to about 450 mg/kg/day, about 0.001 mg/kg/day to about 500 mg/kg/day, about 0.001 mg/kg/day to about 550 mg/kg/day, about 0.001 mg/kg/day to about 600 mg/kg/day, about 0.001 mg/kg/day to about 650 mg/kg/day, about 0.001 mg/kg/day to about 700 mg/kg/day, about 0.001 mg/kg/day to about 750 mg/kg/day, or about 0.001 mg/kg/day to about 800 mg/kg/day. In yet other aspects of this embodiment, an effective amount of a therapeutic compound disclosed herein may be in the range of, e.g., about 0.01 mg/kg/day to about 10 mg/kg/day, about 0.01 mg/kg/day to about 15 mg/kg/day, about 0.01 mg/kg/day to about 20 mg/kg/day, about 0.01 mg/kg/day to about 25 mg/kg/day, about 0.01 mg/kg/day to about 30 mg/kg/day, about 0.01 mg/kg/day to about 35 mg/kg/day, about 0.01 mg/kg/day to about 40 mg/kg/day, about 0.01 mg/kg/day to about 45 mg/kg/day, about 0.01 mg/kg/day to about 50 mg/kg/day, about 0.01 mg/kg/day to about 75 mg/kg/day, about 0.01 mg/kg/day to about 100 mg/kg/day, about 0.01 mg/kg/day to about 150 mg/kg/day, about 0.01 mg/kg/day to about 200 mg/kg/day, about 0.01 mg/kg/day to about 250 mg/kg/day, about 0.01 mg/kg/day to about 300 mg/kg/day, about 0.01 mg/kg/day to about 350 mg/kg/day, about 0.01 mg/kg/day to about 400 mg/kg/day, about 0.01 mg/kg/day to about 450 mg/kg/day, about 0.01 mg/kg/day to about 500 mg/kg/day, about 0.01 mg/kg/day to about 550 mg/kg/day, about 0.01 mg/kg/day to about 600 mg/kg/day, about 0.01 mg/kg/day to about 650 mg/kg/day, about 0.01 mg/kg/day to about 700 mg/kg/day, about 0.01 mg/kg/day to about 750 mg/kg/day, or about 0.01 mg/kg/day to about 800 mg/kg/day. In certain embodiments, an effective amount of a therapeutic compound disclosed herein may be in the range of, e.g., about 0.1 mg/kg/day to about 10 mg/kg/day, about 0.1 mg/kg/day to about 15 mg/kg/day, about 0.1 mg/kg/day to about 20 mg/kg/day, about 0.1 mg/kg/day to about 25 mg/kg/day, about 0.1 mg/kg/day to about 30 mg/kg/day, about 0.1 mg/kg/day to about 35 mg/kg/day, about 0.1 mg/kg/day to about 40 mg/kg/day, about 0.1 mg/kg/day to about 45 mg/kg/day, about 0.1 mg/kg/day to about 50 mg/kg/day, about 0.1 mg/kg/day to about 75 mg/kg/day, about 0.1 mg/kg/day to about 100 mg/kg/day, about 0.1 mg/kg/day to about 150 mg/kg/day, about 0.1 mg/kg/day to about 200 mg/kg/day, about 0.1 mg/kg/day to about 250 mg/kg/day, about 0.1 mg/kg/day to about 300 mg/kg/day, about 0.1 mg/kg/day to about 350 mg/kg/day, about 0.1 mg/kg/day to about 400 mg/kg/day, about 0.1 mg/kg/day to about 450 mg/kg/day, about 0.1 mg/kg/day to about 500 mg/kg/day, about 0.1 mg/kg/day to about 550 mg/kg/day, about 0.1 mg/kg/day to about 600 mg/kg/day, about 0.1 mg/kg/day to about 650 mg/kg/day, about 0.1 mg/kg/day to about 700 mg/kg/day, about 0.1 mg/kg/day to about 750 mg/kg/day, or about 0.1 mg/kg/day to about 800 mg/kg/day. In certain embodiments, an effective amount of a therapeutic compound disclosed herein may be in the range of, e.g., about 10 mg/kg/day to about 15 mg/kg/day, about 10 mg/kg/day to about 20 mg/kg/day, about 10 mg/kg/day to about 25 mg/kg/day, about 10 mg/kg/day to about 30 mg/kg/day, about 10 mg/kg/day to about 35 mg/kg/day, about 10 mg/kg/day to about 40 mg/kg/day, about 10 mg/kg/day to about 45 mg/kg/day, about 10 mg/kg/day to about 50 mg/kg/day, about 10 mg/kg/day to about 75 mg/kg/day, about 10 mg/kg/day to about 100 mg/kg/day, about 10 mg/kg/day to about 150 mg/kg/day, about 10 mg/kg/day to about 200 mg/kg/day, about 10 mg/kg/day to about 250 mg/kg/day, about 10 mg/kg/day to about 300 mg/kg/day, about 10 mg/kg/day to about 350 mg/kg/day, about 10 mg/kg/day to about 400 mg/kg/day, about 10 mg/kg/day to about 450 mg/kg/day, about 10 mg/kg/day to about 500 mg/kg/day, about 10 mg/kg/day to about 550 mg/kg/day, about 10 mg/kg/day to about 600 mg/kg/day, about 10 mg/kg/day to about 650 mg/kg/day, about 10 mg/kg/day to about 700 mg/kg/day, about 10 mg/kg/day to about 750 mg/kg/day, or about 10 mg/kg/day to about 800 mg/kg/day.

In other aspects of this embodiment, an effective amount of a therapeutic compound disclosed herein may be in the range of, e.g., about 1 mg/kg/day to about 10 mg/kg/day, about 1 mg/kg/day to about 15 mg/kg/day, about 1 mg/kg/day to about 20 mg/kg/day, about 1 mg/kg/day to about 25 mg/kg/day, about 1 mg/kg/day to about 30 mg/kg/day, about 1 mg/kg/day to about 35 mg/kg/day, about 1 mg/kg/day to about 40 mg/kg/day, about 1 mg/kg/day to about 45 mg/kg/day, about 1 mg/kg/day to about 50 mg/kg/day, about 1 mg/kg/day to about 75 mg/kg/day, or about 1 mg/kg/day to about 100 mg/kg/day. In certain embodiments, an effective amount of a therapeutic compound disclosed herein may be in the range of, e.g., about 5 mg/kg/day to about 10 mg/kg/day, about 5 mg/kg/day to about 15 mg/kg/day, about 5 mg/kg/day to about 20 mg/kg/day, about 5 mg/kg/day to about 25 mg/kg/day, about 5 mg/kg/day to about 30 mg/kg/day, about 5 mg/kg/day to about 35 mg/kg/day, about 5 mg/kg/day to about 40 mg/kg/day, about 5 mg/kg/day to about 45 mg/kg/day, about 5 mg/kg/day to about 50 mg/kg/day, about 5 mg/kg/day to about 75 mg/kg/day, or about 5 mg/kg/day to about 100 mg/kg/day.

In liquid and semi-solid formulations, a concentration of a therapeutic compound disclosed herein typically may be between about 50 mg/mL to about 1,000 mg/mL. In certain embodiments, a therapeutically effective amount of a therapeutic disclosed herein may be from, e.g., about 50 mg/mL to about 100 mg/mL, about 50 mg/mL to about 200 mg/mL, about 50 mg/mL to about 300 mg/mL, about 50 mg/mL to about 400 mg/mL, about 50 mg/mL to about 500 mg/mL, about 50 mg/mL to about 600 mg/mL, about 50 mg/mL to about 700 mg/mL, about 50 mg/mL to about 800 mg/mL, about 50 mg/mL to about 900 mg/mL, about 50 mg/mL to about 1,000 mg/mL, about 100 mg/mL to about 200 mg/mL, about 100 mg/mL to about 300 mg/mL, about 100 mg/mL to about 400 mg/mL, about 100 mg/mL to about 500 mg/mL, about 100 mg/mL to about 600 mg/mL, about 100 mg/mL to about 700 mg/mL, about 100 mg/mL to about 800 mg/mL, about 100 mg/mL to about 900 mg/mL, about 100 mg/mL to about 1,000 mg/mL, about 200 mg/mL to about 300 mg/mL, about 200 mg/mL to about 400 mg/mL, about 200 mg/mL to about 500 mg/mL, about 200 mg/mL to about 600 mg/mL, about 200 mg/mL to about 700 mg/mL, about 200 mg/mL to about 800 mg/mL, about 200 mg/mL to about 900 mg/mL, about 200 mg/mL to about 1,000 mg/mL, about 300 mg/mL to about 400 mg/mL, about 300 mg/mL to about 500 mg/mL, about 300 mg/mL to about 600 mg/mL, about 300 mg/mL to about 700 mg/mL, about 300 mg/mL to about 800 mg/mL, about 300 mg/mL to about 900 mg/mL, about 300 mg/mL to about 1,000 mg/mL, about 400 mg/mL to about 500 mg/mL, about 400 mg/mL to about 600 mg/mL, about 400 mg/mL to about 700 mg/mL, about 400 mg/mL to about 800 mg/mL, about 400 mg/mL to about 900 mg/mL, about 400 mg/mL to about 1,000 mg/mL, about 500 mg/mL to about 600 mg/mL, about 500 mg/mL to about 700 mg/mL, about 500 mg/mL to about 800 mg/mL, about 500 mg/mL to about 900 mg/mL, about 500 mg/mL to about 1,000 mg/mL, about 600 mg/mL to about 700 mg/mL, about 600 mg/mL to about 800 mg/mL, about 600 mg/mL to about 900 mg/mL, or about 600 mg/mL to about 1,000 mg/mL.

As used herein, "mitigating" means reducing one or more negative symptoms of a condition, relative to a cell, organ, tissue, or organism displaying the symptom or condition for the same amount of time, but untreated.

In some embodiments, contacting the cell, organ, tissue, or organism the present compounds may comprise administering a therapeutically effective amount of the compound to a subject. As used herein, a "therapeutically effective amount" is an amount sufficient to mitigate the negative symptom or condition.

The subject may be a human, rat, mouse, cat, dog, horse, sheep, cow, monkey, avian, or amphibian. In another embodiment, the cell is in vivo or in vitro. Typical subjects to which compounds of the invention may be administered will be mammals, particularly primates, especially humans. For veterinary applications, a wide variety of subjects will be suitable, e.g. livestock such as cattle, sheep, goats, cows, swine and the like; poultry such as chickens, ducks, geese, turkeys, and the like; and domesticated animals particularly pets such as dogs and cats. For diagnostic or research applications, a wide variety of mammals will be suitable subjects including rodents (e.g. mice, rats, hamsters), rabbits, primates, and swine such as inbred pigs and the like. Additionally, for in vitro applications, such as in vitro diagnostic and research applications, body fluids and cell samples of the above subjects will be suitable for use such as mammalian, particularly primate such as human, blood, urine or tissue samples, or blood urine or tissue samples of the animals mentioned for veterinary applications.

When administering to an organism, the compound may be administered by any suitable means. In some embodiments, the compounds or formulations are administered orally. In some embodiments, the compounds or formulations are administered by injection, e.g. subcutaneous, parenteral, or intravenous, injections.

In some embodiments the compound may be administered in combination with other potential mitigators. In a particular embodiment, the composition may be administered with growth factors, NSAIDs, chemotherapeutics, anti-inflammatories, antibiotics, Metformin (Glucophage, Glumetza, others), Sulfonylureas, Meglitinides, Thiazolidinediones, DPP-4 inhibitors, GLP-1 receptor agonists, SGLT2 inhibitors, and/or Insulin therapy, for the treatment of the above conditions. In one aspect, the growth factor can be G-CSF (aka filgrastim, NEUPOGEN®) or erythropoietin (aka EPO-GEN®).

In other embodiments, the compositions may comprise an effective amount of a modulator and/or other pharmaceutically active agent in a physiologically-acceptable carrier. The carrier may take a wide variety of forms depending on the form of preparation desired for a particular route of administration. Suitable carriers and their formulation are described, for example, in Remington's Pharmaceutical Sciences by E. W. Martin. In some embodiments, the compound may be contained in any appropriate amount in any suitable carrier substance, and is generally present in an amount of 1-95% by weight of the total weight of the composition. The composition may be provided in a dosage form that is suitable for parenteral (e.g., subcutaneously, intravenously, intramuscularly, or intraperitoneally) or oral administration route. The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

In some embodiments, the compositions may be in a form suitable for administration by sterile injection. In one example, to prepare such a composition, the compositions(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation may also contain one or more preservatives (e.g., methyl, ethyl or n-propyl p-hydroxybenzoate). For parenteral formulations, the carrier will usually comprise sterile water, though other ingredients, for example, ingredients that aid solubility or for preservation, may be included. Injectable solutions may also be prepared in which case appropriate stabilizing agents may be employed. In one embodiment, the formulation includes at least one or more of methanesulfonic acid, povidone, benzyl alcohol, n-Methyl pyrrolidone, ethaonol, Poloxamer 188, lactic acid, Captisol (SBE-beta-CD), or Vitamin E, such as TPGS (d-alpha tocopheryl polyethylene glycol 1000 succinate).

Formulations suitable for parenteral administration usually comprise a sterile aqueous preparation of the compound, which may be isotonic with the blood of the recipient (e.g., physiological saline solution). Such formulations may include suspending agents and thickening agents and liposomes or other microparticulate systems which are designed to target the compound to blood components or one or more organs. The formulations may be presented in unit-dose or multi-dose form.

Parenteral administration may comprise any suitable form of systemic delivery or localized delivery. Administration may for example be intravenous, intra-arterial, intrathecal, intramuscular, subcutaneous, intramuscular, intra-abdominal (e.g., intraperitoneal), etc., and may be effected by infusion pumps (external or implantable) or any other suitable means appropriate to the desired administration modality.

In some embodiments, the compositions may be in a form suitable for oral administration. In compositions in oral dosage form, any of the usual pharmaceutical media may be employed. Thus, for liquid oral preparations, such as, for example, suspensions, elixirs and solutions, suitable carriers and additives include water, glycols, oils, alcohols, flavoring agents, preservatives, coloring agents and the like. For solid oral preparations such as, for example, powders, capsules and tablets, suitable carriers and additives include starches, sugars, diluents, granulating agents, lubricants, binders, disintegrating agents and the like. If desired, tablets may be sugar coated or enteric coated by standard techniques.

Compositions suitable for oral administration may be presented as discrete units such as capsules, cachets, tablets, or lozenges, each containing a predetermined amount of the active ingredient as a powder or granules. Optionally, a suspension in an aqueous liquor or a non-aqueous liquid may be employed, such as a syrup, an elixir, an emulsion, or a draught. Formulations for oral use include tablets containing active ingredient(s) in a mixture with pharmaceutically acceptable excipients. Such formulations are known to the skilled artisan. Excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

A syrup may be made by adding the compound to a concentrated aqueous solution of a sugar, for example sucrose, to which may also be added any accessory ingredient(s). Such accessory ingredient(s) may include flavorings, suitable preservative, agents to retard crystallization of the sugar, and agents to increase the solubility of any other ingredient, such as a polyhydroxy alcohol, for example glycerol or sorbitol.

In some embodiments, the composition may be in a form of nasal or other mucosal spray formulations (e.g. inhalable forms). These formulations can include purified aqueous solutions of the active compounds with preservative agents and isotonic agents. Such formulations can be adjusted to a pH and isotonic state compatible with the nasal or other mucous membranes. Alternatively, they can be in the form of finely divided solid powders suspended in a gas carrier. Such formulations may be delivered by any suitable means or method, e.g., by nebulizer, atomizer, metered dose inhaler, or the like.

In some embodiments, the composition may be in a form suitable for rectal administration. These formulations may be presented as a suppository with a suitable carrier such as cocoa butter, hydrogenated fats, or hydrogenated fatty carboxylic acids.

In some embodiments, the composition may be in a form suitable for transdermal administration. These formulations may be prepared, for example, by incorporating the active compound in a thixotropic or gelatinous carrier such as a cellulosic medium, e.g., methyl cellulose or hydroxyethyl cellulose, with the resulting formulation then being packed in a transdermal device adapted to be secured in dermal contact with the skin of a wearer.

In addition to the aforementioned ingredients, compositions of the invention may further include one or more accessory ingredient(s) selected from encapsulants, diluents, buffers, flavoring agents, binders, disintegrants, surface active agents, thickeners, lubricants, preservatives (including antioxidants), and the like.

In some embodiments, compositions may be formulated for immediate release, sustained release, delayed-onset release or any other release profile known to one skilled in the art. In some embodiments, the pharmaceutical composition may be formulated to release the active compound substantially immediately upon administration or at any predetermined time or time period after administration. The latter types of compositions are generally known as controlled release formulations, which include (i) formulations that create a substantially constant concentration of the drug within the body over an extended period of time; (ii) formulations that after a predetermined lag time create a substantially constant concentration of the drug within the body over an extended period of time; (iii) formulations that sustain action during a predetermined time period by maintaining a relatively constant, effective level in the body with concomitant minimization of undesirable side effects associated with fluctuations in the plasma level of the active substance (sawtooth kinetic pattern); (iv) formulations that localize action by, e.g., spatial placement of a controlled release composition adjacent to or in the central nervous system or cerebrospinal fluid; (v) formulations that allow for convenient dosing, such that doses are administered, for example, once every one or two weeks; and (vi) formulations that target the site of a pathology. For some applications, controlled release formulations obviate the need for frequent dosing to sustain activity at a medically advantageous level.

Any of a number of strategies can be pursued in order to obtain controlled release in which the rate of release outweighs the rate of metabolism of the compound in question. In one example, controlled release is obtained by appropriate selection of various formulation parameters and ingredients, including, e.g., various types of controlled release compositions and coatings. Thus, the compound is formulated with appropriate excipients into a pharmaceutical composition that, upon administration, releases the compound in a controlled manner. Examples include single or multiple unit tablet or capsule compositions, oil solutions, suspensions, emulsions, microcapsules, microspheres, molecular complexes, nanoparticles, patches, and liposomes.

In some embodiments, the composition may comprise a "vectorized" form, such as by encapsulation of the compound in a liposome or other encapsulate medium, or by fixation of the compound, e.g., by covalent bonding, chelation, or associative coordination, on a suitable biomolecule, such as those selected from proteins, lipoproteins, glycoproteins, and polysaccharides.

In some embodiments, the composition can be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing, agents. Alternatively, the compound may be incorporated in biocompatible carriers, implants, or infusion devices.

Materials for use in the preparation of microspheres and/or microcapsules are, e.g., biodegradable/bioerodible polymers such as polygalactin, poly-(isobutyl cyanoacrylate), poly(2-hydroxyethyl-L-glutamine) and, poly(lactic acid). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(lactic acid), poly (glycolic acid) or poly(ortho esters) or combinations thereof).

In all embodiments, the compound or other active compounds may be present as pharmaceutically acceptable salts or other derivatives, such as ether derivatives, ester derivatives, acid derivatives, and aqueous solubility altering derivatives of the active compound. Derivatives include all individual enantiomers, diastereomers, racemates, and other isomers of the compounds. Derivatives also include all polymorphs and solvates, such as hydrates and those formed with organic solvents, of the compounds. Such isomers, polymorphs, and solvates may be prepared by methods known in the art, such as by regiospecific and/or enantioselective synthesis and resolution.

The ability to prepare salts depends on the acidity or basicity of the compounds. Suitable salts of the compounds include, but are not limited to, acid addition salts, such as those made with hydrochloric, hydrobromic, hydroiodic, perchloric, sulfuric, nitric, phosphoric, acetic, propionic, glycolic, lactic pyruvic, malonic, succinic, maleic, fumaric, malic, tartaric, citric, benzoic, carbonic, cinnamic, mandelic, methanesulfonic, ethanesulfonic, hydroxyethanesulfonic, benezenesulfonic, p-toluene sulfonic, cyclohexanesulfamic, salicyclic, p-aminosalicylic, 2-phenoxybenzoic, and 2-acetoxybenzoic acid; salts made with saccharin; alkali metal salts, such as sodium and potassium salts; alkaline earth metal salts, such as calcium and magnesium salts; and salts formed with organic or inorganic ligands, such as quaternary ammonium salts.

Additional suitable salts include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate salts of the compounds.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

Unless the context clearly indicates otherwise, compositions of all embodiments can comprise various pharmaceutically acceptable salts, or other derivatives described above.

The formulation and preparation of such compositions are well known to those skilled in the art of pharmaceutical formulation. Formulations can be found in Remington: The Science and Practice of Pharmacy.

The amount of the compound employed in the present invention to be used varies according to the condition, the patient/subject, and the extent of the condition.

The contents of all cited references (including literature references, issued patents, published patent applications) as cited throughout this application are hereby expressly incorporated by reference. The invention and the manner and process of making and using it, are described in such full, clear, concise and exact terms as to enable any person skilled in the art to which it pertains, to make and use the same.

The term "unit dosage form" or "unit" as used herein refers to physically discrete units suitable as unitary dosages for human and animal subjects, each unit containing a predetermined quantity of the compound calculated in an amount sufficient to produce the desired effect in association with a pharmaceutically acceptable, diluent, carrier or vehicle. The specifications for the novel unit dosage forms of the present invention depend on the particular compound employed and the effect to be achieved, and the pharmacodynamics associated with each compound in the subject.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

Dosing can be single dosage or cumulative (serial dosing), and can be readily determined by one skilled in the art. For instance, treatment may comprise a one-time administration of an effective dose of a pharmaceutical composition disclosed herein. Alternatively, treatment may comprise multiple administrations of an effective dose of a pharmaceutical composition carried out over a range of time periods, such as, e.g., once daily, twice daily, thrice daily, once every few days, or once weekly. The timing of administration can vary from individual to individual, depending upon such factors as the severity of an individual's symptoms. For example, an effective dose of a pharmaceutical composition disclosed herein can be administered to an individual once daily for an indefinite period of time, or until the individual no longer requires therapy. A person of ordinary skill in the art will recognize that the condition of the individual can be monitored throughout the course of treatment and that the effective amount of a pharmaceutical composition disclosed herein that is administered can be adjusted accordingly.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

In certain embodiments, the period of administration of a therapeutic compound is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In certain embodiments, a treatment regimen may comprise a period during which administration is stopped for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more.

The patient receiving this treatment is any animal in need, including primates, in particular humans, and other mammals such as equines, cattle, swine and sheep; and poultry and pets in general.

In other embodiments, the compounds described herein may be provided with the one or more additional therapeutic agents in a kit, e.g., as separate pharmaceutical formulations capable of being used together in a conjoint therapy as discussed herein, either together in a single container or in separate containers. In certain such embodiments, the kit may further include instructions for the conjoint administration of the pharmaceutical formulations, e.g., for treating or preventing any of the conditions discussed above.

Such combination products may employ compounds of this invention, or pharmaceutically acceptable salts thereof, within the dosage range described hereinbefore and the other pharmaceutically-active agent within its approved dosage range.

In some embodiments, the compound may be administered after the predicate event, such as after exposure to ionizing radiation, or after the initiation of exposure to radiation including accidental or therapeutic radiation. In one embodiment, the compound is administered immediately after the exposure. In another embodiment, the compound is administered within 12 hours of the exposure. In another embodiment, the compound is administered within 24 hours of the exposure. In another embodiment, the compound is administered at 24 hours after the exposure. In another embodiment, the compound is administered after 24 hours of exposure. In another embodiment, the compound is administered after 36 hours of exposure. In another embodiment, the compound is administered within 48 hours of exposure. In another embodiment, the compound is administered within 60 hours of exposure. In another embodiment, the compound is administered within 72 hours of the exposure. In another embodiment, the compound is administered within 84 hours of the exposure.

The invention now being generally described, it will be more readily understood by reference to the following examples which are included merely for purposes of illustration of certain aspects and embodiments of the present invention and are not intended to limit the invention.

Examples

The following non-limiting examples are provided for illustrative purposes only in order to facilitate a more complete understanding of representative embodiments now contemplated. These examples should not be construed to limit any of the embodiments described in the present specification, including those pertaining to the compounds, pharmaceutical compositions, or methods and uses disclosed herein.

Compound 512 Will Mitigate RIGS and Improve Survival Following Lethal Dose of Radiation Lethality from Acute Radiation Syndrome (ARS) depends upon dose dependent injury to various organs. Total body exposure to a radiation dose higher than 8 Gy results in mortality within 15 days post exposure, primarily due to RIGS. Intestinal epithelium is highly radio-sensitive because of its rapid self-renewal rate compared to any other organ. Every 4-5 days a new epithelium takes charge for mucosal defense under very strict epithelial homeostasis. High doses of radiation disrupt this homeostatic balance, kill ISCs and impair the repair process, resulting complete loss of mucosal barrier within 5-10 days post-exposure.

512 Mitigates Radiation Injury in Human Lung Organoids

Human non-malignant pulmonary surgical specimens were collected from KUMC biorepository and then used to develop lung organoids. Human lung organoids receiving irradiation demonstrated significant loss in budding structure. However, treatment with 512 rescued those organoids from radiation toxicity improves the budding structure.

Figure 2:
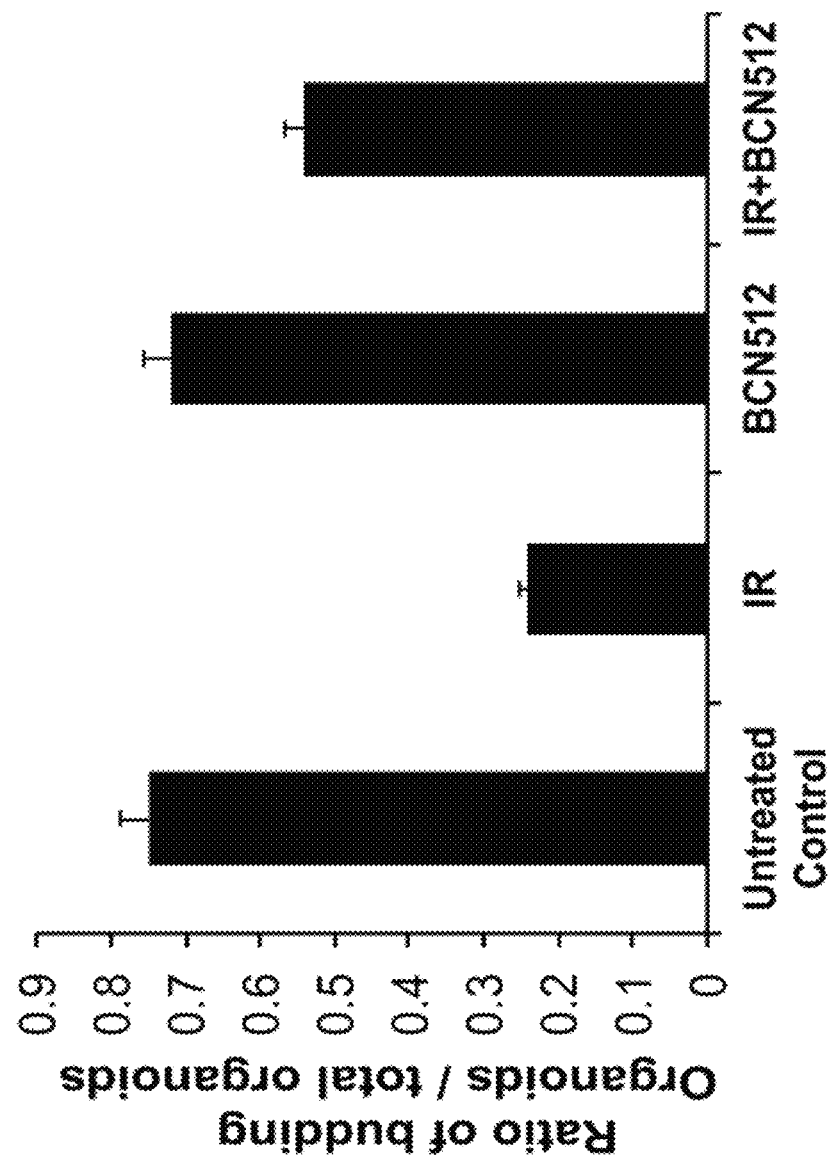
FIG. 2 is a view of a histogram demonstrating the higher budding organoid to total organoid ratio compared to an irradiated control.

FIGS. 1 and 2 illustrate that 512 mitigates radiation toxicity in human pulmonary organoids. Lung organoids were developed from human non-malignant surgical specimen of lung. Organoids were grown in ALI culture. FIG. 1: Note loss of budding structure in these organoids in response to radiation exposure. However, treatment with 512 after radiation exposure rescued these organoids from radiation toxicity and improves budding structure. FIG. 2: Histogram demonstrating the higher budding organoid to total organoid ratio compared to irradiated control (p<0.004) (unpaired two tailed t test).

To examine the radio-mitigating role of 512 against RIGS, C57BI6 mice are exposed to graded doses of abdominal irradiation (AIR) (14-15 Gy) after shielding the thorax, head and neck, and extremities, thus protecting the bone marrow. A single fraction of 14-15 Gy AIR induces RIGS and lethality in 100% of animals within 7-12 days post-exposure. Mice will receive 512 at 24 hrs post AIR and are expected to continue to survive beyond 30 days post-exposure without showing any symptoms of RIGS. These results will indicate that 512 mitigates the lethal radiation injury in intestine.

Unless there has been a very focal radiation exposure there will also be involvement of many other organ systems, and their differential responses to various doses of irradiation will impact the gastrointestinal acute radiation syndrome (GI-ARS) dose response. All radiation doses inducing GI-ARS will have a major impact on the bone marrow, which in turn will affect the levels of intestinal inflammation and ability of the body to manage the infection resulting from bacterial translocation through an impaired intestinal mucosal barrier.

TABLE 1

| Cytokine | Ctl | LTI | LTI + 512 |
| --- | --- | --- | --- |
| IL-6 | 7 | 15 | 88 |
| KC | 10 | 210 | 245 |
| MCP-1 | 17 | 103 | 77 |
| IL-1b | 32 | 50 | 7 |
| MIP-1b | 25 | 88 | 13 |
| IL-23 | 13 | 79 | 23 |

Table 1 shows plasma cytokine levels in rodents treated with 5 mg/kg 512 and plasma cytokines tested. Ctl, control with no treatment. LTI, lower thoracic radiation, LTI+512, radiation, and 512. The cytokine phenotype is anti-inflammatory where IL-6 is an anti-inflammatory cytokine required for controlling local or systemic acute inflammatory responses and IL-1 is pro inflammatory and so forth.

To investigate involvement of bone marrow in survival outcome upon 512 treatment, C57BI6 mice will be exposed to partial body irradiation (PBI) where 40% of total bone marrow is exposed (BM40) to irradiation after shielding head and fore limbs. Treatment with 512 at 24 hrs post exposure of 14.5 Gy PBI will rescue mice from radiation lethality. This data will indicate that 512 will rescue GI epithelium from GI epithelium even in absence of protective function from bone marrow (BM).

Compound 512 Will not Protect Malignant Tissue from Radiation

Compound 512 was examined in the National Cancer Institute (NCI) 60 cancer cell line platform. Several of these cell lines are known to be positive for dysregulation of the Wnt/b-catenin signaling pathway. None of these cancer cells will show any proliferative response to 512 treatment unlike normal tissue.

Figure 3:
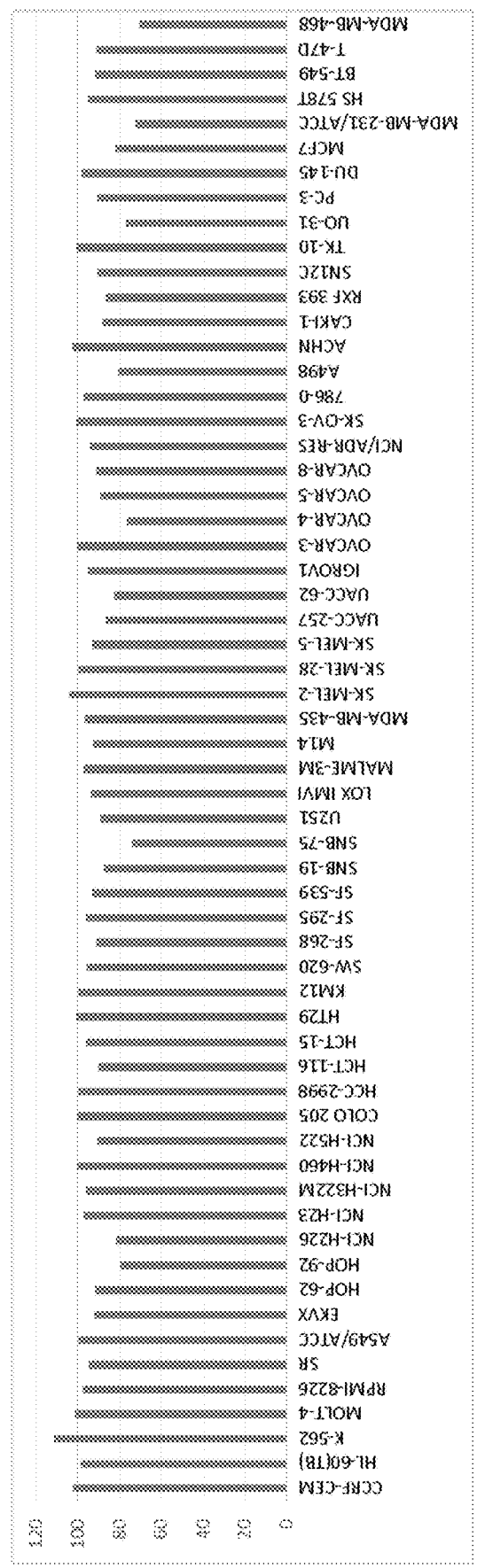
FIG. 3 is a chart showing NCI 60 cancer cell screening with annotations for cancer cell lines used in the assay with 512.

NCI 60 cancer cell screening with annotations for cancer cell lines used in the assay. Each data point represents the percent growth over control which is only vehicle treated (DMSO) as presented with FIG. 3. The data clearly indicate that 512 does not promote tumor growth.

These results indicate that 512 can also be used as adjuvant therapy to minimize the toxic side effects of abdominal radiotherapy.

512 Activates Canonical WNT-β Catenin Signaling

Figure 4:
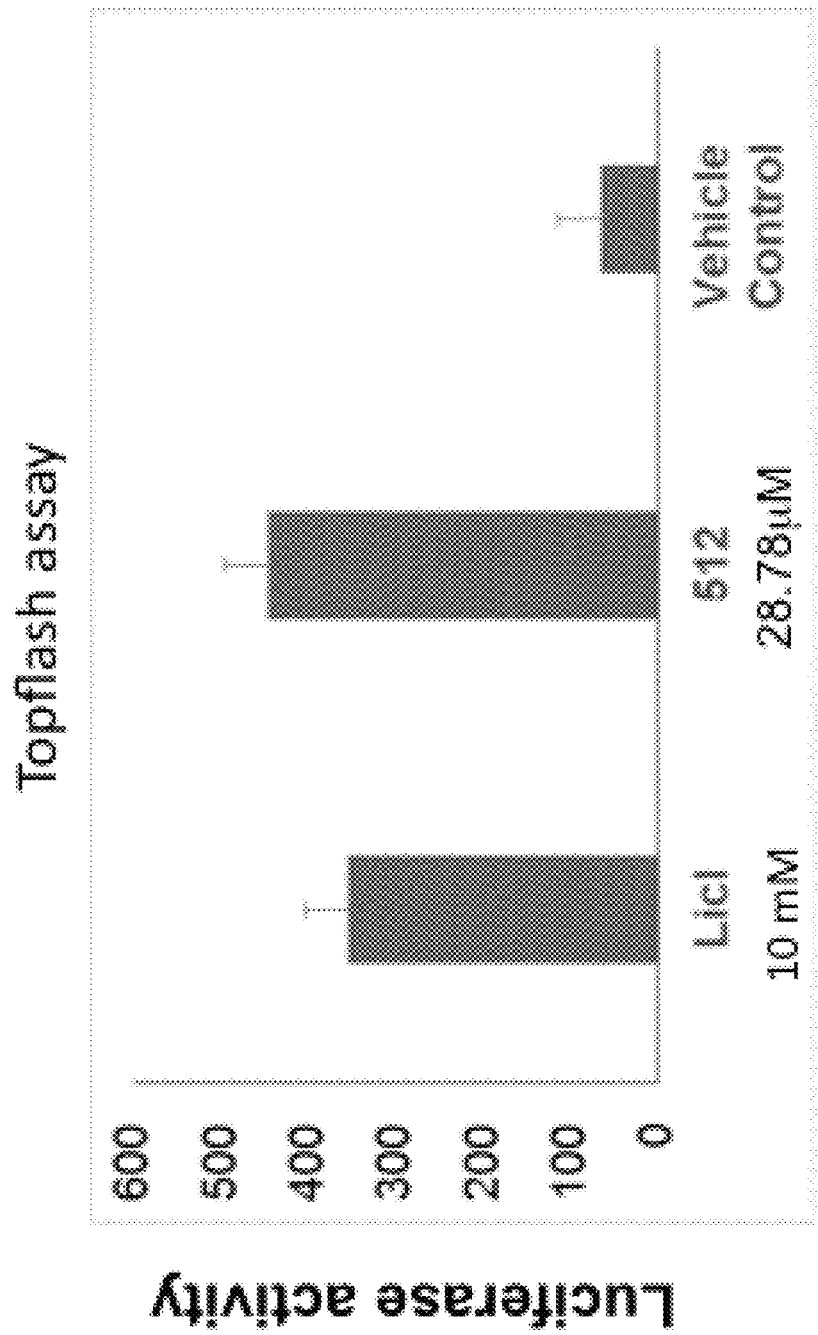
FIG. 4 is a chart showing 512 treatment significantly increases luciferase activity in HEK293 cells compared to vehicle treated cells.

To determine the canonical WNT activity in 512 (28.78 µM) HEK293 cells having TCF/LEF luciferase reporter construct were treated with 512 or vehicle control. LiCl (10 mM) treatment was used as positive control for luciferase activity. Luciferase activity was determined 24 hr after using Dual-Luciferase® Reporter Assay System (Promega) as per manufacturer's protocol. HEK293 cells having FOPFLASH construct were used as negative control. 512 treatment as presented with FIG. 4, significantly increases luciferase activity in HEK293 cells compared to vehicle treated cells. LiCl used as positive control also demonstrated significant increase in Luciferase activity. WNT-β catenin signaling is well known to promote the self renewal and differentiation of LGR5+ epithelial (lung, oral, intestinal) stem cells.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular compound, composition, article, apparatus, methodology, protocol, and/or reagent, etc., described herein, unless expressly stated as such. In addition, those of ordinary skill in the art will recognize that certain changes, modifications, permutations, alterations, additions, subtractions and sub-combinations thereof can be made in accordance with the teachings herein without departing from the spirit of the present specification. It is therefore intended that the following appended claims and claims hereafter introduced are interpreted to include all such changes, modifications, permutations, alterations, additions, subtractions and sub-combinations as are within their true spirit and scope.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. For instance, as mass spectrometry instruments can vary slightly in determining the mass of a given analyte, the term "about" in the context of the mass of an ion or the mass/charge ratio of an ion refers to +/−0.50 atomic mass unit. At the very least, and not as an attempt to limit the application of the doctrine of equivalents to the scope of the claims, each numerical indication should at least be construed in light of the number of reported significant digits and by applying ordinary rounding techniques.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar references used in the context of describing the present invention (especially in the context of the following claims) are to be construed to cover both the singular and the plural, unless otherwise indicated herein or clearly contradicted by context. Further, ordinal indicators—such as "first," "second," "third," etc.—for identified elements are used to distinguish between the elements, and do not indicate or imply a required or limited number of such elements, and do not indicate a particular position or order of such elements unless otherwise specifically stated. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

When used in the claims, whether as filed or added per amendment, the open-ended transitional term "comprising" (and equivalent open-ended transitional phrases thereof like including, containing and having) encompasses all the expressly recited elements, limitations, steps and/or features alone or in combination with unrecited subject matter; the named elements, limitations and/or features are essential, but other unnamed elements, limitations and/or features may be added and still form a construct within the scope of the claim. Specific embodiments disclosed herein may be further limited in the claims using the closed-ended transitional phrases "consisting of" or "consisting essentially of" in lieu of or as an amended for "comprising." When used in the claims, whether as filed or added per amendment, the closed-ended transitional phrase "consisting of" excludes any element, limitation, step, or feature not expressly recited in the claims. The closed-ended transitional phrase "consisting essentially of" limits the scope of a claim to the expressly recited elements, limitations, steps and/or features and any other elements, limitations, steps and/or features that do not materially affect the basic and novel characteristic(s) of the claimed subject matter. Thus, the meaning of the open-ended transitional phrase "comprising" is being defined as encompassing all the specifically recited elements, limitations, steps and/or features as well as any optional, additional unspecified ones. The meaning of the closed-ended transitional phrase "consisting of" is being defined as only including those elements, limitations, steps and/or features specifically recited in the claim whereas the meaning of the closed-ended transitional phrase "consisting essentially of" is being defined as only including those elements, limitations, steps and/or features specifically recited in the claim and those elements, limitations, steps and/or features that do not materially affect the basic and novel characteristic(s) of the claimed subject matter. Therefore, the open-ended transitional phrase "comprising" (and equivalent open-ended transitional phrases thereof) includes within its meaning, as a limiting case, claimed subject matter specified by the closed-ended transitional phrases "consisting of" or "consisting essentially of." As such embodiments described herein or so claimed with the phrase "comprising" are expressly or inherently unambiguously described, enabled and supported herein for the phrases "consisting essentially of" and "consisting of."

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Lastly, the terminology used herein is for the purpose of describing particular embodiments only and is not intended to limit the scope of the present invention, which is defined solely by the claims. Accordingly, the present invention is not limited to that precisely as shown and described.

What is claimed is:

1. A method of treating chemotherapy induced injury or radiation induced injury of the GI tract in a subject in need thereof, the method comprising the step of administering to the subject a therapeutically effective amount of a compound of Formula IIA:

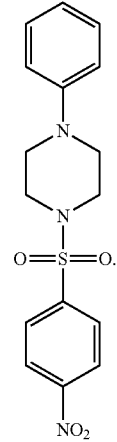

Formula IIA

2. The method of claim 1, wherein the compound is administered to the subject within 48 hours of the radiation exposure.

3. The method of claim 1, wherein the compound is administered to the subject after 24 hours of the radiation exposure.

4. The method of claim 1, wherein the subject received radiation therapy or chemotherapy.

5. The method of claim 1, wherein the injury of the GI tract is identified as one or more of radiation-induced gastrointestinal syndrome (RIGS), radiation-induced mucositis, radiation-induced proctitis or radiation-induced enteritis.

6. The method of claim 1, wherein the injury of the GI tract is identified as one or more of chemotherapy-induced gastrointestinal syndrome, chemotherapy-induced mucositis, chemotherapy-induced proctitis or chemotherapy-induced enteritis.

7. A method of treating chemotherapy induced injury or radiation induced injury of the GI tract in a subject in need thereof, the method comprising the step of administering to the subject a therapeutically effective amount of an analog of Formula IIA, wherein the analog is selected from the group consisting of Formula IIC, Formula IID, Formula IIE and Formula IIB:

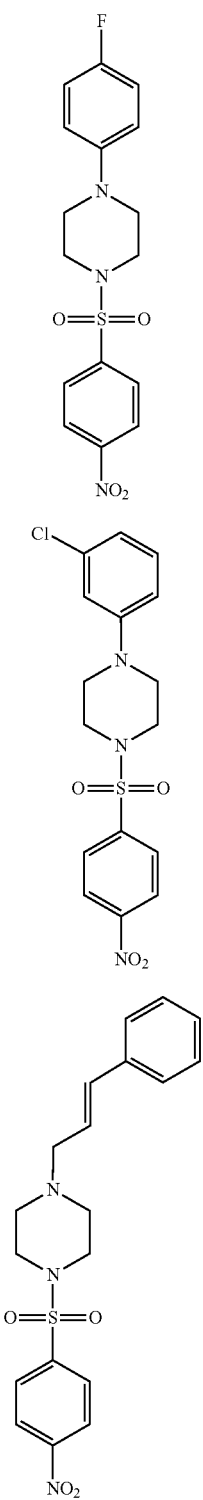

Formula IIC

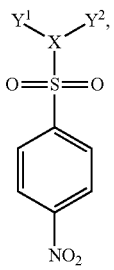

Formula IIB wherein $Y^1$ and $Y^2$ taken together with X form:

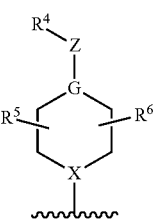 or 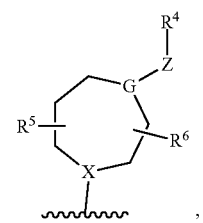,

Formula IID                Formula IIE wherein X is N, G is N, Z is absent or selected from substituted or unsubstituted alkyl, heteroalkyl, alkenyl, or alkynyl, wherein $R^4$ is absent or selected from substituted or unsubstituted aryl; and wherein $R^5$ and $R^6$ are each independently absent or lower alkyl.

8. The method of claim 7, wherein the compound is administered to the subject within 48 hours of the radiation exposure.

9. The method of claim 7, wherein the compound is administered to the subject after 24 hours of the radiation exposure.

10. The method of claim 7, wherein the subject received radiation therapy or chemotherapy.

11. The method of claim 7, wherein the injury of the GI tract is identified as one or more of radiation-induced gastrointestinal syndrome (RIGS), radiation-induced mucositis, radiation-induced proctitis or radiation-induced enteritis.

12. The method of claim 7, wherein the injury of the GI tract is identified as one or more of chemotherapy-induced gastrointestinal syndrome, chemotherapy-induced mucositis, chemotherapy-induced proctitis or chemotherapy-induced enteritis.

* * * * *